United States Patent [19]

Kokubo et al.

[11] Patent Number: 5,008,113
[45] Date of Patent: Apr. 16, 1991

[54] METHOD FOR PREPARING FILM COATED PHARMACEUTICAL PREPARATIONS AND METHOD FOR IMPROVING PROPERTIES THEREOF

[75] Inventors: Hiroyasu Kokubo, Joetu; Fujio Sekigawa, Omiya; Tohru Chiba, Joetsu; Yoshiro Onda, Higashikurume, all of Japan

[73] Assignee: Shin-Etsu Chemical Co., Ltd., Tokyo, Japan

[21] Appl. No.: 355,110

[22] Filed: May 19, 1989

Related U.S. Application Data

[63] Continuation of Ser. No. 148,000, Jan. 25, 1988, abandoned.

[30] Foreign Application Priority Data

Jan. 28, 1987 [JP] Japan .................................. 62-17846
Jan. 28, 1987 [JP] Japan .................................. 62-17847

[51] Int. Cl.$^5$ .............................................. A61K 9/36
[52] U.S. Cl. ..................................... 424/480; 424/464; 424/490
[58] Field of Search .................... 424/464, 490, 480; 427/541

[56] References Cited

U.S. PATENT DOCUMENTS

| | | | |
|---|---|---|---|
| 4,360,541 | 11/1982 | Costanza et al. | 427/54.1 |
| 4,411,754 | 10/1983 | Kaetsu et al. | 424/78 |
| 4,524,060 | 6/1985 | Mughal et al. | 424/459 |
| 4,539,060 | 9/1985 | Wittwer et al. | 156/275.1 |

Primary Examiner—Merrell C. Cashion, Jr.
Assistant Examiner—Leon R. Horne
Attorney, Agent, or Firm—Parkhurst, Wendel & Rossi

[57] ABSTRACT

Film coated pharmaceutical preparations, which are prepared by overlaying to the outer surface of pharmaceutical preparations, a coating layer comprising at least one member selected from the group consisting of methyl cellulose, hydroxypropylmethyl cellulose, hydroxypropyl cellulose, hydroxypropylmethyl cellulose phthalate, hydroxypropylmethyl cellulose acetate succinate, carboxymethylethyl cellulose and cellulose acetate phthalate, are irradiated with light including ultraviolet rays. Whereby film coated pharmaceutical preparations, the coating layer surface of which are excellent in whiteness, are prepared. Moreover, as a content of a white pigment in corporated into the coating layer of such preparations may be reduced, the stability of such preparations can be enhanced without impairing the strength of the coating layer.

5 Claims, No Drawings

METHOD FOR PREPARING FILM COATED PHARMACEUTICAL PREPARATIONS AND METHOD FOR IMPROVING PROPERTIES THEREOF

This is a continuation of application Ser. No. 07/148,000 filed Jan. 25, 1988, now abandoned.

BACKGROUND OF THE INVENTION

The present invention relates to a method for preparing film coated pharmaceutical preparations composed of a solid drug and a coating layer on the outer surface thereof and a method for improving properties of film coated pharmaceutical preparations likewise comprised of a solid drug and a coating layer on the outer surface thereof, which makes it possible to impart an excellent appearance to the film coated pharmaceutical preparations.

Heretofore, solid drugs such as tablets have been subjected to film coating treatment to form film coated pharmaceutical preparations therefrom. Such a coated film serves to prevent uncomfortable tastes of drugs from giving out therefrom, as well as to protect effective components of the drugs from causing property change and to control the releasing behaviors of the effective components in the digestive system after an administration thereof. In view of enhancing the reliability of drugs and the acceptability of their appearance as medicines, it has been desired to impart a snow white and beautiful finish to such a coating layer. In some cases, coated films are pigmented by incorporating, into the basic materials (basic coating materials) for forming the coating layer, a coloring material during the film coating operations. In such a case, it is desired for the coated film to have a finish of a bright color tone.

However, the basic materials conventionally employed are slightly gray colored or yellow colored ones and thus it has been very difficult to obtain snow white basic coating materials. If a film coated pharmaceutical preparations are prepared utilizing such a basic coating material, the color of the resultant coating layer thereof is not completely white but they are slightly pigmented. On the other hand, if a coloring material is incorporated into the basic coating material, the color of the resultant coating layer of the film coated pharmaceutical preparations is not clear because of the influence of the color of the basic coating material. Therefore, the acceptability of the visual appearance of the drugs is greatly reduced and the commercial value thereof is also lowered due to such coloration.

Furthermore, a white pigment has been incorporated into the basic coating material to improve the whiteness thereof. However, the use of such white pigment leads to the reduction of the strength of the coating layer, which in turn leads to undesirable releasing behavior and possible property change of the effective components.

SUMMARY OF THE INVENTION

Accordingly, it is a general purpose of the present invention to effectively eliminate the aforementioned drawbacks asociated with the conventional film coated pharmaceutical preparations.

More specifically, it is a primary purpose of the present invention to provide a method for preparing film coated pharmaceutical preparations composed of a drug and a coated layer thereon, the layer of which has a high strength and is excellent in a whiteness thereof or a clearness of a color thereof.

It is another purpose of the present invention to provide a method for improving properties of previously produced, film coated pharmaceutical preparations, which makes it possible to enhance a whiteness or a clearness of a pigmented color of the coated preparations without exerting any adverse influence on the strength of the coating layer.

The inventors of the present invention have conducted various studies on substances constituting basic coating materials to be applied to the surface of drugs to obtain film coated pharmaceutical preparations. As a result, the inventors have found that, for instance, in the case of hydroxypropylmethyl cellulose used as the basic coating material, the color thereof in the solid state has a close corelation with the color of the aqueous solution thereof and the color of the aqueous solution, in turn, has a close corelation with the ultraviolet absorption properties thereof. In other words, though the aqueous solution of the basic coating material is tinged with yellow, the yelowish color of the solution is reduced by irradiating it with light including ultraviolet rays having a wave length of around 278 nm, due to the absorption thereof. The basic coating material in the solid state obtained by solidifying the aqueous solution thus prepared exhibits almost snow white. The present invention has been completed on the basis of such a finding.

Consequently, according to the first aspect of the present invention, there is provided a method for preparing pharmaceutical preparations having coated films thereon, which have a high strength and a high whiteness or high clearness of the color thereof and the method comprises overlaying, to the outer surface of drugs, a coating layer comprising at least one member selected from the group consisting of methyl cellulose (MC), hydroxypropylmethyl cellulose (HPMC), hydroxypropyl cellulose (HPC), hydroxypropylmethyl cellulose phthalate (HPMCP), hydroxypropylmethyl cellulose acetate succinate (HPMCAS), carboxymethylethyl cellulose (CMEC) and cellulose acetate phthalate (CAP) and then drying, while irradiating with light including ultraviolet rays.

In this respect, the irradiation of the preparations with light including ultraviolet rays may be effected during the coating procedure or the drying procedure or further throughout the coating and drying operations.

According to another aspect of the present invention, there is provided a method for improving properties of previously produced, film coated pharmaceutical preparations without impairing the strength of the coated film and the method comprises irradiating, with light including ultraviolet rays, the film coated pharmaceutical preparations having, on the outer surface thereof, coated films comprised of at least one member selected from the group consisting of methyl cellulose (MC), hydroxypropylmethyl cellulose (HPMC), hydroxypropyl cellulose (HPC), hydroxypropylmethyl cellulose phthalate (HPMCP), hydroxypropylmethyl cellulose acetate succinate (HPMCAS), carboxymethylethyl cellulose (CMEC) and cellose acetate phthalate (CAP).

According to a further aspect of the present invention, there is provided a method for improving properties of previously produced pharmaceutical preparations having coated films on the outer surface thereof and the method comprises irradiating, with light including ultraviolet rays, the film coated pharmaceutical preparations having coating films, which comprise at lease one member selected from the group consisting of methyl cellulose (MC), hydroxypropylmethyl cellulose (HPMC), hydroxypropyl cellulose (HPC), hydroxypropylmethyl cellulose phthalate (HPMCP), hydroxypropylmethyl cellulose acetate succinate (HPMCAS), carboxymethylethyl cellulose (CMEC) and cellulose acetate phthalate (CAP), containing at least 0.3% of moisture.

DETAILED EXPLANATION OF THE INVENTION

According to the method for preparing film coated pharmaceutical preparations of this invention, a coating liquid is first prepared by dissolving or dispersing, in a solvent, the foregoing basic coating material together with necessary additives such as plasticizers and pigments in order to form a coating layer on the outer surface of drugs.

The aforementioned substances are coventionally known ones as the basic coating materials for applying a coating film onto the outer surface of phermaceutical preparations and they are also preferably used in the methods according to the present invention.

Examples of such solvents used for preparing a coating liquid, which may be employed in this invention include water, organic solvents or the mixture thereof. In a coating liquid to obtain pharmaceutical preparations having colored coating films, dyes are in general incorporated into the coating solution. As dyes used in method of this invention, there may be mentioned such coloring materials as a variety of edible dyes, lake dyes and red iron oxide and it is preferred to use red iron oxide, becouse of its high stability to light.

The formation of coating film on the outer surface of the pharmaceutical preparations may be effected in accordance with any known coating methods.

According to the method for preparing the film coated pharmaceutical preparations of the present invention, the preparations are irradiated with light including ultraviolet rays therein during the formation of the coating films. The irradiation with the light can also be carried out during drying operation and throughout the coating and drying operations as already explained above. The irradiation time and the strength of the light irradiated may be controlled according to need.

As the coating apparatuses which may be used in the method of this invention, there may be mentioned such a conventionally known apparatus as a pan coating apparatus, a coating machine provided with an air flow drying mechanism and a fluidized coating machine. On the other hand, as the method for irradiating the pharmaceutical preparations during processing with the light, there may be employed a method which comprises disposing a light source within, for instance, the pan of the pan coating appatatus and rotating the pan to stir the preparations and to ensure the uniform and effective irradiation of the pharmaceutical preparations with the light. Light sources may be disposed within the fluidized bed.

Ultraviolet rays included in the light, with which the film coated pharmaceutical preparations is irradiated, are not restricted to specific range, however, it is preferably those having a wave length of 200 nm to 380 nm. Examples of light sources, which emit such light including ultraviolet rays, are sunlight, mercury lamps such as low pressure mercury lamp, high pressure mercury lamp and superhigh pressure mercury lamp, fluorescent tube, a halogen lamp and xenon lamp. Among these, preferred are mercury lamps having a high spectral strength in ultraviolet region. For instance, the peak wave length of the low pressure mercury lamp is equal to 253.7 nm while that of the high pressure mercury lamp is 365.0 nm.

The present invention further relates to a method for improving properties of film coated pharmaceutical preparations not yet irradiated with the light including ultraviolet rays.

In order to irradiate finished film coated pharmaceutical preparations with the light including ultraviolet rays, there may be employed, in this invention, a method comprising, for example, placing the film coated pharmaceutical preparations on a belt conveyor and passing the preparations through an irradiated region while turning round the preparations on the belt conveyor or a method comprising rotating or stirring the film coated pharmaceutical preparations contained in a container such as a coating pan while irradiating these preparations with the light. In any cases, it should be needed to uniformly irradiate the surface of the film coated preparations with the light.

Thus, according to the method of this invention, the whiteness of the coating layer of the film coated pharmaceutical preparations are surely improved by irradiating the basic coating material selected from the foregoing materials with light including ultraviolet rays. The reason therefor is not necessarily clear, however, it may be possible to consider as follows. That is, the film coated pharmaceutical preparations which have not been irradiated with light including ultraviolet rays look like yellow due to the absorption of the light by the conjugated double bonds present in the substances which constitute the basic coating materials, while if the pharmaceutical preparations are irradiated with the light including ultraviolet rays, the conjugated double bonds thereof partially undergo oxidation reaction schematically shown below and thus the conjugated double bond system is destroyed:

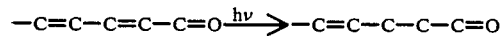

Therefore, the absorption band is shifted towards the low wave length region in accordance with such destruction of the conjugated double bond system and, as a result, the yellowish color of the coating layer is disappeared. For this reason, it is believed that the white color is more and more close to snow white while the pigmented color exhibits a clear and beautiful finish.

Accordingly, the film coated pharmaceutical preparations exhibiting an enhanced whiteness can be prepared even if a pigment such as titanium oxide is incorporated thereinto only in a small amount. This, in turn, makes it possible to prevent the lowering of the film strength of the coating layer. This is quite preferred on the viewpoint of the stability of film coated pharmaceutical preparations and thus it is possible to prevent the effective components contained therein from causing property change due to the destruction of the coating layer.

The method according to the present invention is hereinbefore explained with reference to solid pharmaceutical preparations, in particular, tablets, however, the methods of this invention is effectively applicable to other solid pharmaceutical preparations such as those in the form of granules and powder.

The methods according to the present invention will hereunder be explained in more detail with reference to the following working non-limitative examples and the effects practically acheived will also be discussed in detail in comparison with comparative examples.

EXAMPLE 1

A low pressure mercury lamp (manufactured and sold by USHIO ELECTRIC CO., LTD. under the trade name of ULO-6DQ power=6 W) was disposed in a pan coating apparatus (manufactured and sold by FREUND INDUSTRIES CO., LTD. under the trade name of FM-2). While aqueous solution of 6% HPMC (available from SHIN-ETSU CHEMICAL CO., LTD. under the trade name of Pharamacoat 606 was prepared. Then, 2 kg of white tablets mainly composed of lactose and starch, each having a diameter of 8 mm and a weight of 200 mg, were coated with the HPMC aqueous solution, so that the coated amount per a tablet is 8 mg, in the foregoing pan coating apparatus while irradiating them with light from the low pressure mercury lamp to thus obtain film coated tablets B (Sample of the present invention).

On the other hand, 2 kg of the aforementioned white tablets were likewise coated with the same coating liquid so as to form a coating film of 8 mg per a tablet, utilizing the fregoing pan coating apparatus without the irradiation of the light to obtain film coated tablets A (Comparative Sample).

The film coated tablets A and B thus prepared were inspected on Y I, i.e., yellowness index employing SM COLOR COMPUTOR (trade name: available from SUGA TESTING MACHINE CO., LTD.). In this connection, the yellowness index YI can be estimated by determining the three components' excitation values (x,y,z) and substituting these values into the following equation:

$$YI = 100(1.28x - 1.06z)/y$$

As a result, the yellowness index YI of the film coated tablets A was 10.5 while that of the film coated tablets B was equal to 6.5. Therefore, the film coated tablet prepared according to the present invention had a whiteness higher than that of the Comparative Sample.

EXAMPLE 2

Coating of white talets mainly composed of lactose and starch, each having a diameter of 8 mm and a weight of 200 mg per a tablet, was effected using HPMCAS (manufactured and sold by SHIN-ETSU CHEMICAL CO., LTD. under the trade name of AQOAT AS-MF) under the following conditions:

| Formulation of the Coating Liquid | |
|---|---|
| AQOAT AS-MF | 10 parts |
| Triethyl citrate | 3 parts |
| Water | ad. 100 parts in total |

Coating method

A low pressure mercury lamp having 20 W power (manufactured and sold by USHIO ELECTRIC CO., LTD. under the trade name of ULI-2DQ) was set on a 24 inches Accela-Cota (trade name: manufactured and sold by MANESTY CO. in England) to provide a coating machine. Utilizing this coating machine, 10 kg of the foregoing white tablets were coated so as to form film coated tablets having a coated film of 22 mg per a tablet without irradiating them with the light to obtain film coated tablets C. Likewise, 10 kg of the aforementioned white tablets were coated using the same coating machine while irradiating them with the light from the low pressure mercury lamp to obtain film coated tablets having coated films of 22 mg per a tablet to obtain film coated tablets D. Further, 10 kg of the aforementioned white tablets were coated utilizing the same coating machine while irradiating them with the light from the low pressure mercury lamp to form coating film of 22 mg per a tablet followed by drying while continuing the irradiation with the light to obtain film coated tablets E.

The yellowness indexes YI of these film coated tablets C, D and E, which were determined according in the same manner as in Example 1, were 12.3, 7.2 and 5.1 respectively. Thus, the film coated tablets D and E prepared according to the method of this invention exhibited high whitenesses compared with the films coated tablets C being Comparative one.

EXAMPLE 3

White tablets mainly comprised of lactose and hydoxypropyl cellulose of low degree of substitution (standard product in accordance with Japanese Pharmacopoeia), each having a diameter of 8 mm and a weight of 200 mg per a tablet, were coated with 6% aqueous solution of HPMC (available from SHIN-ETSU CHEMICAL CO., LTD. under the trade name of Pharamacoat 606: Japanese Pharmacopoeia hydroxypropylmethyl cellelose 2910) to obtain film coated tablets F having coating films of 8 mg per a tablet.

2 kg of the film coated tablets F were charged into a pan of the pan coating machine (manufactured and sold by FREUND INDUSTRIES CO., LTD. under the trade name of FM-2) provided with a 6 W low pressure mercury lamp (manufactured and sold by USHIO ELECTRIC CO., LTD. under the trade name of ULO-6DQ) therein and they were stirred by rotating the pan at 8 rpm for 2 hours while irradiating them with the light from the mercury lamp and thus form film coated tablets G. Thereafter, the yellowness index YI was determined on the film coated tablets F and G thus prepared according in the same manner as in Example 1.

As a result, it was found that the film coated tablets F which were not irradiated with the light exhibited the yellowness index YI of 10.5 while that of the film coated tablets G irradiated with the light was 6.8. This clearly showed that the method for improving properties of the film coated pharmaceutical preparations according to the present invention surely made it possible to enhance the color of the coated preparations. In this respect, the moisture content of the film coated tablets irradiated with the light was 1.8%.

EXAMPLE 4

2 kg of film coated tablets F, which were obtained according in the same manner as in Example 3 and which were not irradiated with the light, were fluidized by injecting air at a rate of 2.0 m³/min. at room temperature in Glatt fluidized coating apparatus (manufactured and sold by OKAWARA SEISAKUSHO CO. under the trade name of WSG-1) and simultaneously irradiating them with the light from a 6 W low pressure mercury lamp disposed above the tablets for 1 hour to obtain film coated tablets H. Film coated tablets I were likewise prepared according in the same manner except that the tablets were irradiated with the light for 2 hours. According in the same manner as in Example 1, the yellowness indexes YI of the film coated tablets H and I were determined and found to be 7.1 and 6.0 respectively. Moreover, the moisture contents thereof were 1.6% and 1.3% respectively.

EXAMPLE 5

Coating of white tablets mainly composed of lactose and hydroxypropyl cellulose of low degree of substitution (standard product in accordance with Japanese Pharmacopoeia), each having a diameter of 8 mm and a weight of 200 mg per a tablet were effected using HPMCAS (manufactured and sold by SHIN-ETSU CHEMICAL CO., LTD. under the trade name of AQOAT AS-MF) under the following conditions:

| Formulation of the Coating Liquid | |
| --- | --- |
| AQOAT AS-MA | 10 parts |
| Triethyl citrate | 3 parts |
| Water | ad. 100 parts in total |

Coating method 10 kg of white tablets were coated so as to form film coated tablets having a coated film of 22 mg per a tablet (film coated tablets J) using 24 inches Accela-Cota (trade name: manufactured and sold by MANESTY CO. in England). The film coated tablets J were irradiated with the light from a 20 W low pressure mercury lamp (manufactured and sold by USHIO ELECTRIC CO., LTD. under the trade name of ULI-2DQ) set on the coating machine to obtain film coated tablets K. The yellowness indexes YI of these film coated tablets J and K, which were determined according in the same manner as in Example 1, were 12.3 and 7.50, respectively. In addition, the moisture content thereof were 2.5% and 2.6% respectively.

EXAMPLE 6

2 kg of the film coated tablets, which were not irradiated with the light and were prepared in Example 5, were charged into the pan of the pan coating apparatus FM-2 provided with a 6 W low pressure mercury lamp therein and the tablets were stirred by rotating the pan at 8 rpm while irradiating them with the light from the mercury lamp for 2 hours to prepare film coated tablets L. The yellowness index YI of the tablets L thus prepared was 7.50 and the moisture content thereof was 2.6%.

EXAMPLE 7

The film coated tablets F, which were not irradiated with the light including ultraviolet rays and were prepared in Example 3, were dried in a vacuum desiccator to obtain film coated tablets differing in their moisture contents, i. e., film coated tablets Mo (moisture content =0.22%): film coated tablets No (moisture content=0.45%): film coated tablets Oo (moisture content=0.81%): and film coated tablets Po (moisture content=1.3%). The yellowness indexes YI were determined on these film coated tablets without irradiating with the light and found to be 10.1 for thetablets Mo, 10.3 for the tablets No, 10.4 for the tablets Oo and 10.4 for the tablets Po respectively.

According in the same manner as in Example 3, the film coated tablets Mo, No, Oo and Po were irradiated with the light including ultraviolet rays and thus film coated and light irradiated tablets M, N, O and P were obtained. The yellowness indexes thereof were 9.8, 7.4, 7.2 and 6.9 respectively. These results clearly evidence that more the moisture content in the non-irradiated, film coated tablets, the higher the yellowness improving effect due to the irradiation with the light.

What is claimed is:

1. A method for providing white colored film coated pharmaceutical preparations, said method comprising the steps of providing pharmaceutical preparations having a film coating material containing moisture, and irradiating said film coating with ultra violet rays to partially oxidize the material to a Yellowness Index in the range of about 5.1 to 9.8, wherein said film coating material comprises at least one member selected from the group consisting of methyl cellulose, hydroxypropylmethyl cellulose, hydroxypropyl cellulose, hydroxypropylmethyl cellulose phthalate, hydroxypropylmethyl cellulose acetate succinate, carboxymethyl cellulose and cellulose acetate phthalate.

2. The method of claim 1 wherein said ultraviolet rays have a wavelength in the range of 200 nm to 380 nm.

3. The method of claim 1 wherein said mositure content is at least 0.3 percent.

4. The method of claim 1 wherein said moisture content is at least 1.3 percent.

5. The method of claim additionally comprising drying during the irradiating.

* * * * *